United States Patent
Dutu et al.

(10) Patent No.: US 10,610,589 B2
(45) Date of Patent: Apr. 7, 2020

(54) METHOD AND APPARATUS FOR CREATING STRUCTURED WATER BY EXPOSING WATER TRANSVERSAL AND LONGITUDINAL TO ULTRA- LOW FREQUENCY ELECTROMAGMETIC FIELDS

(71) Applicants: Iulius Vivant Dutu, Boca Raton, FL (US); Sara Julia Dutu, Boca Raton, FL (US)

(72) Inventors: Iulius Vivant Dutu, Boca Raton, FL (US); Sara Julia Dutu, Boca Raton, FL (US)

(*) Notice: Subject to any disclaimer, the term of this patent is extended or adjusted under 35 U.S.C. 154(b) by 43 days.

(21) Appl. No.: 15/949,413

(22) Filed: Apr. 10, 2018

(65) Prior Publication Data

US 2018/0221484 A1 Aug. 9, 2018

Related U.S. Application Data

(63) Continuation-in-part of application No. 15/670,958, filed on Aug. 7, 2017, now Pat. No. 10,505,993,
(Continued)

(51) Int. Cl.
*A61K 41/00* (2020.01)
*A61K 41/10* (2020.01)
(Continued)

(52) U.S. Cl.
CPC .............. *A61K 41/00* (2013.01); *A61K 35/08* (2013.01); *A61K 41/0004* (2013.01);
(Continued)

(58) Field of Classification Search
CPC .. C02F 1/48; C02F 1/487; C02F 1/488; C02F 1/58; C02F 5/00; C02F 5/02; C02F 5/06;
(Continued)

(56) References Cited

U.S. PATENT DOCUMENTS

| 6,203,710 B1 * | 3/2001 | Woodbridge | A61L 2/02 204/155 |
| 2002/0056666 A1 * | 5/2002 | Sharaf | C02F 1/481 209/214 |

(Continued)

FOREIGN PATENT DOCUMENTS

| JP | 2005046723 A | * | 2/2005 | C02F 1/44 |
| WO | WO-2001019736 A1 | * | 3/2001 | C02F 1/48 |

(Continued)

*Primary Examiner* — Nam X Nguyen
*Assistant Examiner* — Ekandra S. Miller-Cruz
(74) *Attorney, Agent, or Firm* — Daniel S. Polley, P.A.

(57) ABSTRACT

An apparatus and method is provided for healing and regeneration of live human and animal bodies and influencing interaction and intercommunication at the cellular level. The apparatus can include one or more environmental and/or body sensors. An electrical circuit can also be provided to produce a square or trapezoidal wave that is delivered to a transducer for application, preferably timed at specific frequencies Delta, Theta, Alpha, to Beta, based on information received from the one or more sensors. In certain embodiments, a DC power source can be provided which allows the apparatus to be portable. A wireless communication module can also be provided. An apparatus and method for structuring water is also disclosed.

20 Claims, 17 Drawing Sheets

Related U.S. Application Data which is a continuation-in-part of application No. 14/550,176, filed on Nov. 21, 2014, now Pat. No. 9,724,535, which is a continuation-in-part of application No. 13/957,979, filed on Aug. 2, 2013, now abandoned.

(60) Provisional application No. 61/766,226, filed on Feb. 19, 2013.

(51) Int. Cl.

| | | |
|---|---|---|
| *C02F 1/00* | (2006.01) | |
| *A61K 35/08* | (2015.01) | |
| *A61N 2/06* | (2006.01) | |
| *C02F 1/48* | (2006.01) | |
| *C02F 1/68* | (2006.01) | |
| *A61N 2/02* | (2006.01) | |

(52) U.S. Cl.
CPC ............... *A61K 41/10* (2020.01); *C02F 1/001* (2013.01); *C02F 1/005* (2013.01); *A61N 2/02* (2013.01); *A61N 2/06* (2013.01); *C02F 1/481* (2013.01); *C02F 1/484* (2013.01); *C02F 1/487* (2013.01); *C02F 1/68* (2013.01); *C02F 2201/48* (2013.01); *C02F 2209/006* (2013.01)

(58) Field of Classification Search
CPC ............ C02F 2209/055; C02F 2303/08; C02F 1/485; C02F 2303/22; C02F 2103/42; C02F 2101/10; C02F 1/005; C02F 1/001; C02F 2201/48; C02F 1/484; C02F 1/68; C02F 2209/006; C02F 1/481; B03C 1/0335; B03C 1/288; B03C 2201/18; H01F 5/00; H01F 7/06; H01F 7/123; H01F 17/0033; H01F 17/04; H01F 17/045; H01F 27/28; H01F 38/22; H01F 38/38; H01F 27/40; H01F 27/2823; H01F 27/24; A61K 41/00; A61K 41/0004; A61K 35/08; A61K 41/0009; A61N 2/06; A61N 2/02

USPC .. 210/167.1, 167.03, 167.29, 222, 687, 695; 335/213, 220, 230, 250, 289, 299

See application file for complete search history.

(56) References Cited

U.S. PATENT DOCUMENTS

| | | | | |
|---|---|---|---|---|
| 2004/0118782 | A1* | 6/2004 | Allen | C02F 1/487 |
| | | | | 210/695 |
| 2016/0251762 | A1* | 9/2016 | Sehner | C23G 1/00 |
| | | | | 210/695 |

FOREIGN PATENT DOCUMENTS

| | | | | |
|---|---|---|---|---|
| WO | WO-2014138011 A1 * | 9/2014 | | C02F 1/48 |
| WO | WO-2014173672 A1 * | 10/2014 | | C02F 1/481 |

\* cited by examiner

METHOD AND APPARATUS FOR CREATING STRUCTURED WATER BY EXPOSING WATER TRANSVERSAL AND LONGITUDINAL TO ULTRA- LOW FREQUENCY ELECTROMAGMETIC FIELDS

This application is a Continuation-In-Part of U.S. application Ser. No. 15/670,958, filed Aug. 7, 2017, which is a Continuation-In-Part of U.S. application Ser. No. 14/550,176, filed Nov. 21, 2014, now U.S. Pat. No. 9,724,535, which is a Continuation-In-Part of U.S. application Ser. No. 13/957,979, filed Oct. 2, 2013, which claims priority to and the benefit of U.S. Application Ser. No. 61/766,226, filed Feb. 19, 2013. All applications are incorporated by reference in their entireties for all purposes.

BACKGROUND OF THE DISCLOSURE

Magnetic influence on living bodies has been known for a long time starting from ancient Greece and Egypt and is currently used as a therapeutic technique in different ways, including with permanent magnets to pulse an electromagnetic field. Research into magnetic therapy proves the health benefits in living bodies. As a result, the number of people who sleep on magnetic beds and/or who wear magnets during the day is continually increasing. These uses have shown the energy increase on bodies and have achieved success in the healing process.

It turns out that pulse magnetic frequencies appear to act as a whole-body battery recharger by pumping and priming the cells of the body. The cells in the body are similar to little wet batteries that operate ideally at around 70 millivolts. The membrane acts like a one-way rectifier that converts the earth's magnetic pulse intro electrical potential energy, which charges the body cells. This energy drives cell metabolism and enhances oxygenation, improves absorption of nutrition and essential elements into the cell and can help to remove waste out of the cell. The entire process of regeneration and healing has used frequencies and energy of the planet Earth, namely the Schumann resonant frequencies and the Earth's magnetic field.

Though directly magnetically influencing a living body is known, magnetically influencing items consumed by a living body for therapeutic and health purposes is unknown. The present disclosure is directed to a novel device and method for addressing these shortcomings.

SUMMARY OF THE DISCLOSURE

Disclosed is an apparatus for enhancing regenerative, recovery and healing of a living body. The disclosed embodiments preferably comprise at least one environmental and/or body sensor connected to an electrical circuit, which applies a preferred, but not limiting, trapezoidal or square wave varying electrical current to a transducer at a different frequency to generate an electromagnetic field output.

The disclosed apparatus preferably changes the frequency from Delta, Theta, Alpha to Beta (1 Hz-30 Hz) based on the sensor(s) and will produce an electromagnetic force intensity of about 0.001 to about 0.45 Gauss, continuously forever how long the supplied power is present. The disclosed apparatus preferably can generate a same or highly similar type of energy that exist and is created by planet earth.

Thus, the disclosed embodiments provide for a method and apparatus for regenerative, recovery and healing for live humans and animals by applying a low frequency of an electromagnetic pulse which can be varied based on one or more environmental and/or body conditions and which influence interaction and intercommunication at the cellular level for biological organisms and molecular level of matter.

Also, disclosed is an apparatus and method for structured water, providing a novel process mimicking a natural water cycle using electromagnetic pulses varying the ultra-low frequencies, and field intensity. In a preferred embodiment, two or three stages of water filtration can be provided along with preferably two types of magnetization of the water, namely, transversal or perpendicular and longitudinal or parallel to the water flow through the device, apparatus or system. Preferably the magnetization is simultaneous and continuous.

Using the novel disclosed apparatus and method, the magnetized water is biologically active and can therefore have a therapeutic effect. A certain position of the dipoles of water molecules in a magnetic field longitudinal and transversal to the field lines can be maintained, thus making the water more structured and orderly, as the water being subjected to an electromagnetic magnetic field becomes structured.

The low frequency magnetized water increases the solubility of minerals and therefore improves the transfer of nutrients to all parts of the body, making the organisms work more efficiently. It increases the rate of crystallization and chemical reactions of solutes. It also intensifies the process of adsorption, coagulation of impurities and improves their loss in the sediment. After exposing water to the magnetic field, the water becomes more structured than ordinary water. Exposure of the water to a low frequency magnetic field with the disclosed apparatus and method influences the behavior of the impurities present in it. Biological effects to the body, from the structured water are also possible from the channels of cell membranes of tissue being passed by structured water molecules with increased speed, such that the regular structure of the water itself can resemble a regular structure of the cell membrane.

The structure of the magnetic water helps it faster and easier to penetrate cells and act on them. Thus, the improved water through use of the disclosed apparatus and method can possibly have antibacterial properties, cleanse the blood vessels of foreign proteins, reduce the amount of cholesterol in the blood and liver, increase metabolism, promote soft fragmentation of gallstones and kidney stones, regulates blood pressure and increase the tone of the body and stimulate the immune system, and possibly assist in cell regeneration.

DETAILED DESCRIPTION

Figure 1:
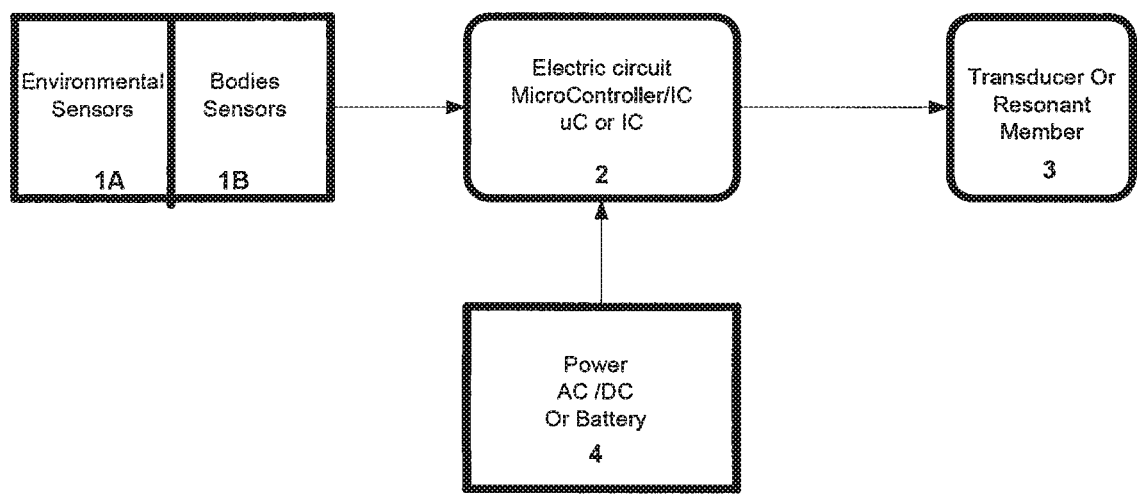
FIG. 1 is a block diagram of the main components for one embodiment of the energy generating apparatus in accordance with the disclosure.

The several embodiments for the disclosed apparatus will be more fully described below, but is not limited by the attached figures and ensuing description in which:

In FIG. 1 blocks 1A and 1B represent the one or more sensors that can be used with the disclosed apparatus, with Block 1A used to denote one or more environmental sensor(s), such as, but not limited to, barometric pressure sensor, temperature sensor, oxygen level sensor, photo sensor, etc. One or more multiple sensors or embodied sensor (such as a MPL115A2 sensor, though not limiting, which in one miniature foot print can read the barometric pressure and temperature) can be used in the apparatus for supplying information which will be used to vary the frequency and/or electromagnetic intensity. Block 1B shows the one or more sensors that can be attached to or located approximate to or near a live body and can read, without limitation, body temperature, heartbeat, pH level, etc.

One or multiple environmental sensors (1A) and/or body sensors (1B) can be in communication with an electrical circuit which is preferably run by a microcontroller or regular integrated circuit ("IC") (block 2). The circuit/microcontroller/IC determines what change to the frequency and/or electromagnetic field intensity has occurred, if any, based on information received from environmental sensor(s) 1a and/or body sensor(s) 1b.

In a more complex embodiment for the apparatus a variety of sensors can be used for providing the information that is used for determining any varying of the frequency and/or the intensity of electromagnetic force. The determination can be based on a programmed algorithm, which will yield the most efficient results for regenerating, balances and healing of a live body. The power (block 4) can be a portable unit with battery(ies) having between about 6 to about 12 volts, and/or a stationary unit using an AC/DC power supply (about 100 to about 240 volt; about 50 Hz to about 60 Hz, to about 6 VDC to about 12 VDC). Block 3 represents the transducer/resonator coil which can be used for supplying conductive coil (based on the output from the microcontroller or IC) which preferably can be in a square or trapezoidal wave form, though such is not considered limiting. The transducer or resonator 3 receives the electric pulse or signal from the electrical circuit 2 and provides or creates a magnetic pulse output. Based on information received from sensors 1A and/or 1B the frequency generated by the electrical circuit can be varied and/or changes can be made to the intensity of the magnetic pulse output from transducer or resonator 3.

Alternatively, the electromagnetic force can be generated by a four axis resonate frequency member preferably composed of four conductive coils placed on each side of a trunk pyramid at approximately ⅔ from the base with both bases being open such that a hand or leg can go through. In another embodiment, the coil sizes can be chosen such that they can encompass an entire live human or animal body. The frequency resonator embodiment shown in FIG. 2 can create a resonant frequency that can provide increased healing and regeneration of live human and animal bodies.

Figure 2:
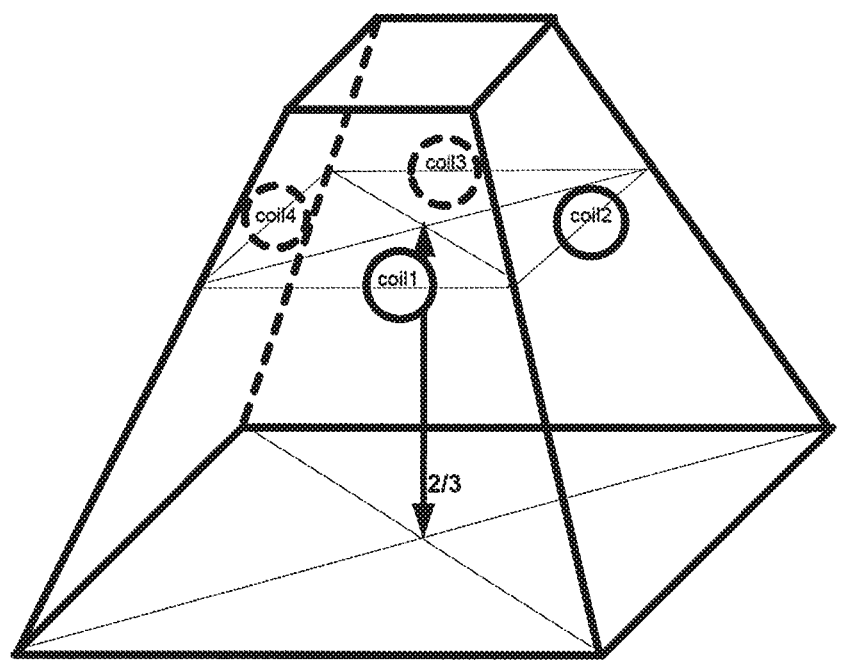
FIG. 2 is an illustration showing one embodiment for the frequency resonator that can be used in accordance with the disclosure.

The frequency resonator shown FIG. 2 can be an electromagnetic resonant assembly preferably compose of four conductive coils connected sequentially to the microcontroller output two sequentially in opposite axis in the same time or all four simultaneous. Other number of conductive coils can also be provided and similarly connected with the microcontroller and are also considered within the scope of the invention.

Figure 3:
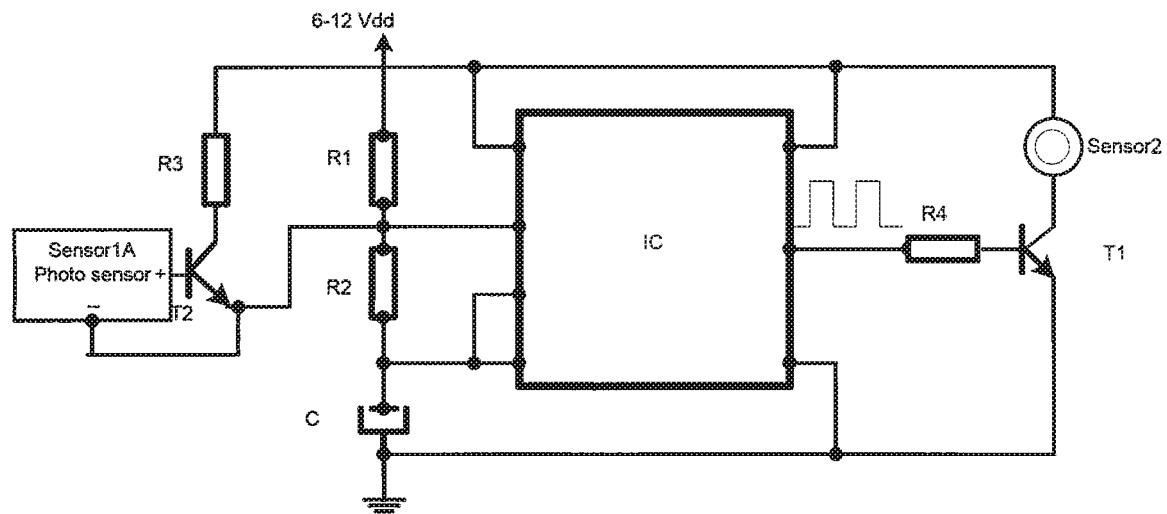
FIG. 3 is an electrical schematic for one embodiment of the disclosed apparatus which is shown using an IC chip and at least one environmental sensor.
Figure 3:
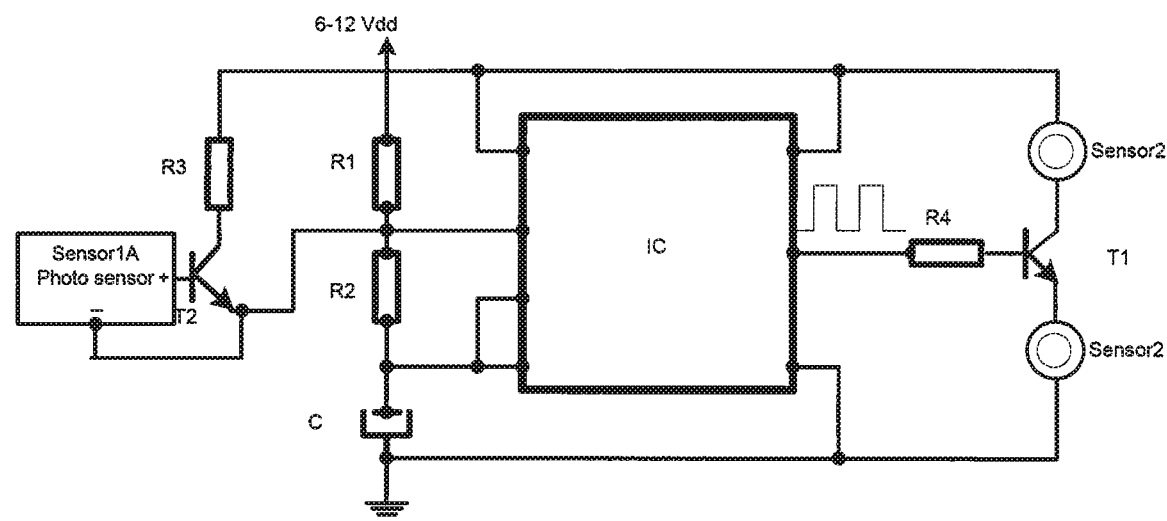

As seen in FIG. 3, one embodiment for an electrical circuit of the apparatus is disclosed for healing and regenerating live human and animal bodies and reveals a first novel example for producing an electromagnetic pulse with a varying frequency, the intensity of the magnetic force and alternating the polarity based on information received from a photo sensor. Though a photo sensor has been shown for the electrical circuit, it should be recognized that other sensors, such as, but not limited to, one or more of the above-mentioned sensors can also be selected in place or in addition to the photo sensor, and use of such other sensors are also considered within the scope of the disclosure.

In this embodiment, in the presence of light a live body usually is in an active stage (awake stage) and the photo sensor can activate transistor T1 causing resistor R3 to be connected in parallel with resistor R1. With transistor T1 activated, the IC circuit generates a frequency in a high alpha-low beta range (about 11 Hz-about 12.5 Hz). In the absence of light or a low intensity of light the living body is usually in a relaxed stage and the photo sensor will not activate the base of transistor T1. Thus, resistor R3 will not be connected to anything and the IC circuit generates a different frequency of a high theta-low alpha range (about 7.7 Hz-about 8.2 Hz).

The IC circuit can be setup and/or programmed to generate two different frequencies which can alternate at a specific time in order to allow the changing of polarity of the electromagnetic field. Each frequency can be changed by information received from any sensor connected to the IC circuit. The above teaching is not considered limiting and is only one non-limiting example for functionality of the disclosed apparatuses and one non-limiting use/method for the regenerative, healing apparatus. Similarly, the above presentation for the operation of the circuit shown in FIG. 3 is also applicable when other types of sensor(s) are connected to the electric circuit.

Figure 4:
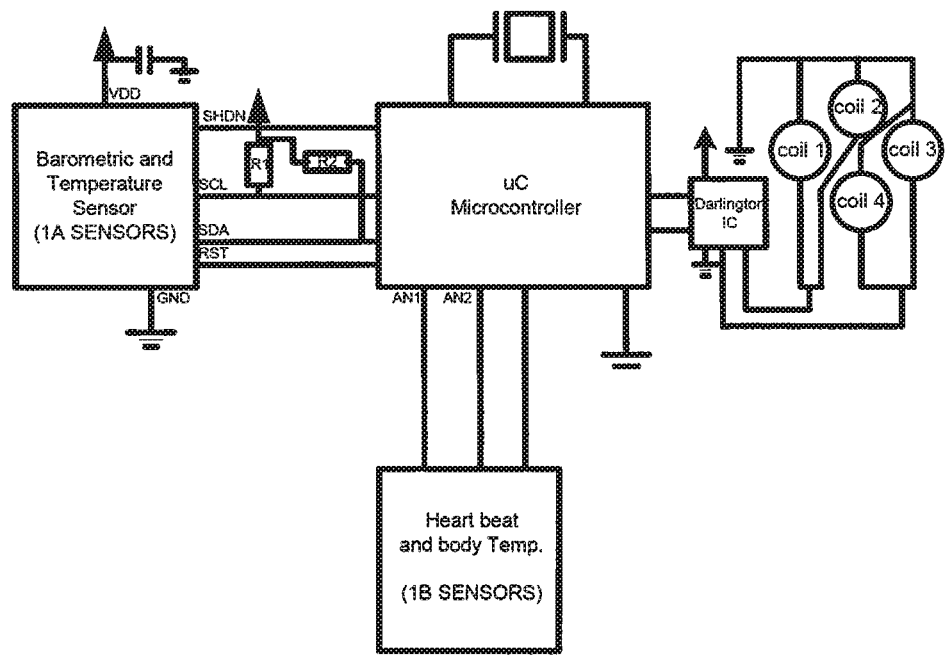
FIG. 4 is an electrical schematic for another embodiment of the disclosure which includes environmental and bodies sensors in communication with a microcontroller and the microcontroller in communication with preferably four transducers/resonators/coils, though the number of transducers/resonators/coils is not considered limiting.

FIG. 4 shows another embodiment for the apparatus for regenerating and healing live human and animal bodies by varying the low frequency and intensity of an electromagnetic field in accordance with environmental and body conditions using an algorithm programmed and stored and running thru a microcontroller.

Figure 5:
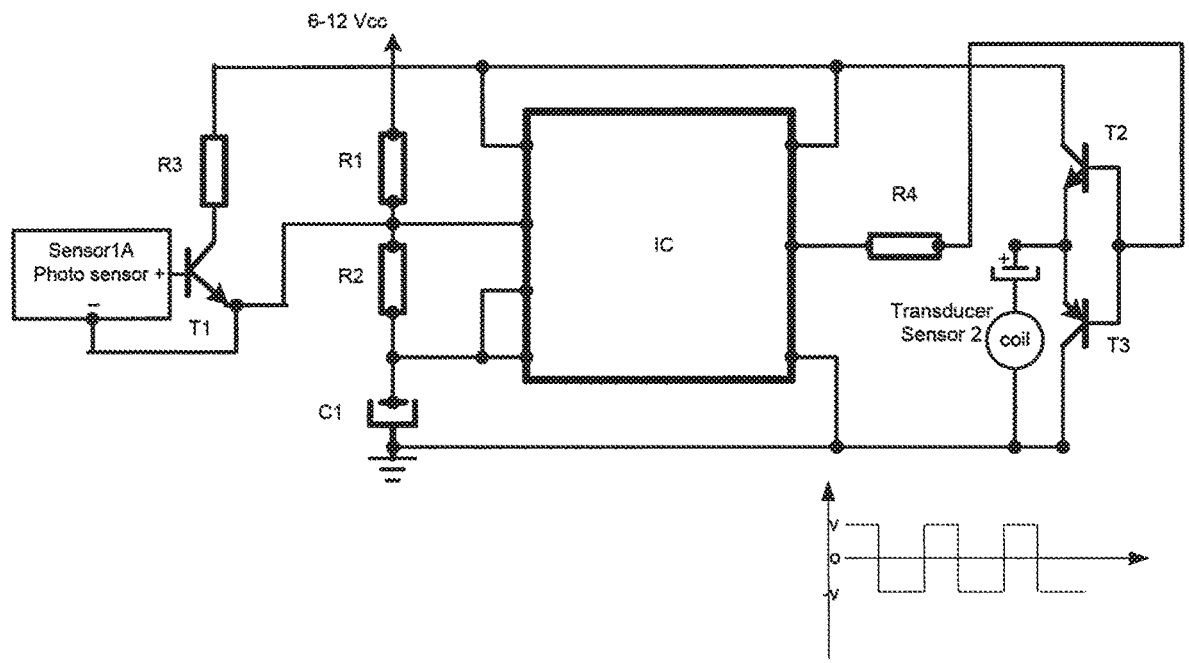
FIG. 5 is an electrical schematic for a further embodiment of the disclosed apparatus using an IC chip and at least one environmental sensor with square wave alternative DC.

FIG. 5 discloses an electrical diagram which produces an alternating DC square wave for its output. Generally, resistors R1 and R2 and capacitor C1 in conjunction with IC chip generate a base frequency. In one embodiment, the IC chip can function as an oscillation circuit. Resistor R3 and transistor T1 can be provided to change, vary or switch the base frequency up or down and also to change the duty cycle which increases or decreases the power of the output accordingly. Resistor R4 can be provided to energize the base of transistors T2 or T3. Transistors T2 and T3 can be provided to amplify the signal received from the IC chip and create differentiation of the DC pulse output, and also determine the polarity of the magnetic field. Other electrical or electronic components that will perform the same functions can be used in replace of any of the above or below described electrical or electronic components. Similar positioned electrical or electronic components shown or described for other embodiments of the apparatus function similar to the functions described in FIG. 5.

Figure 6:
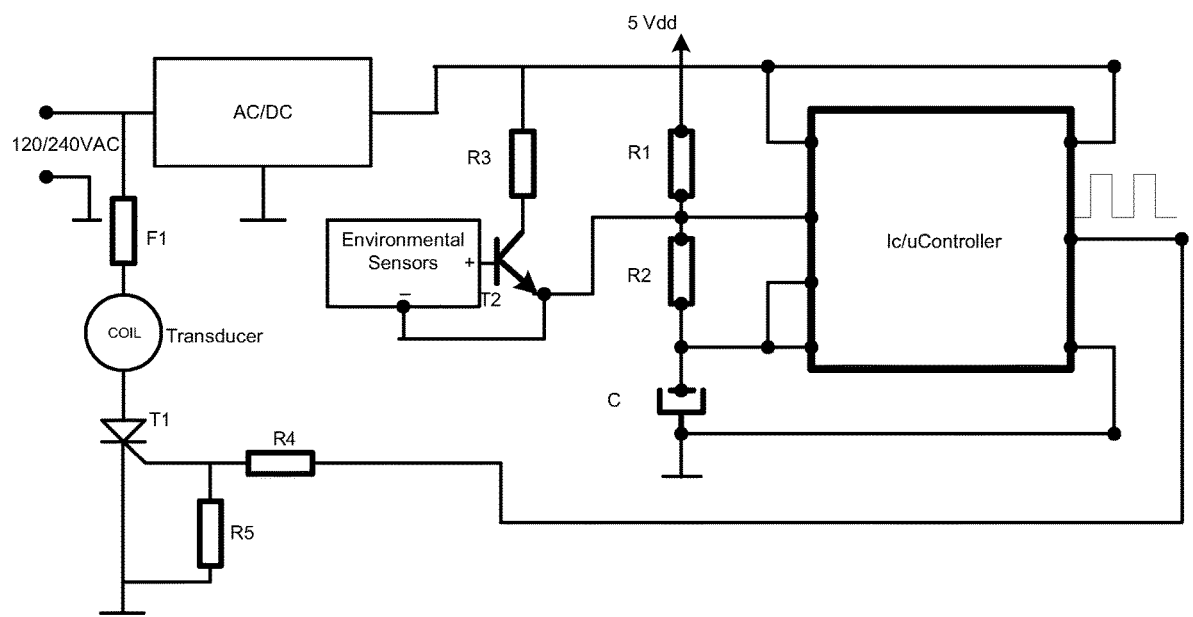
FIG. 6 is an electrical schematic for still another embodiment of the disclosed apparatus preferably using at least one environmental sensor in communication with the IC microcontroller chip, with the output signal from the microcontroller a gate T1 to allow the coil/transducer/resonator to be energized by a high voltage AC circuit and generating a magnetic pulse field.

FIG. 6 discloses an electrical schematic showing one or more environmental sensors that can be used to control and determine the cycles for producing magnetic energy, in connection with any type of 120/240 AC outlet. The circuit can be a low voltage AC to DC circuit, which can be made with discrete components or by integrating a AC to DC converter, providing for an output for about 5 V DC for the IC oscillator or microcontroller. The output of the IC or microcontroller will generate train square pulses determined by the environmental sensors. The square pulses can be applied to the gate of TRIAC (T1). Based on the environmental sensors, the signal cycles sent to the gate of TRIAC T1 allows the high voltage to pass through the transducer producing the pulsed magnetic energy and allows the alternating current (with a frequency preferably between about 47 to about 65 Hz) to pass through the transducer at a preferred frequency of about 7 to about 30 Hz as dictated by the sensors.

Figure 7:
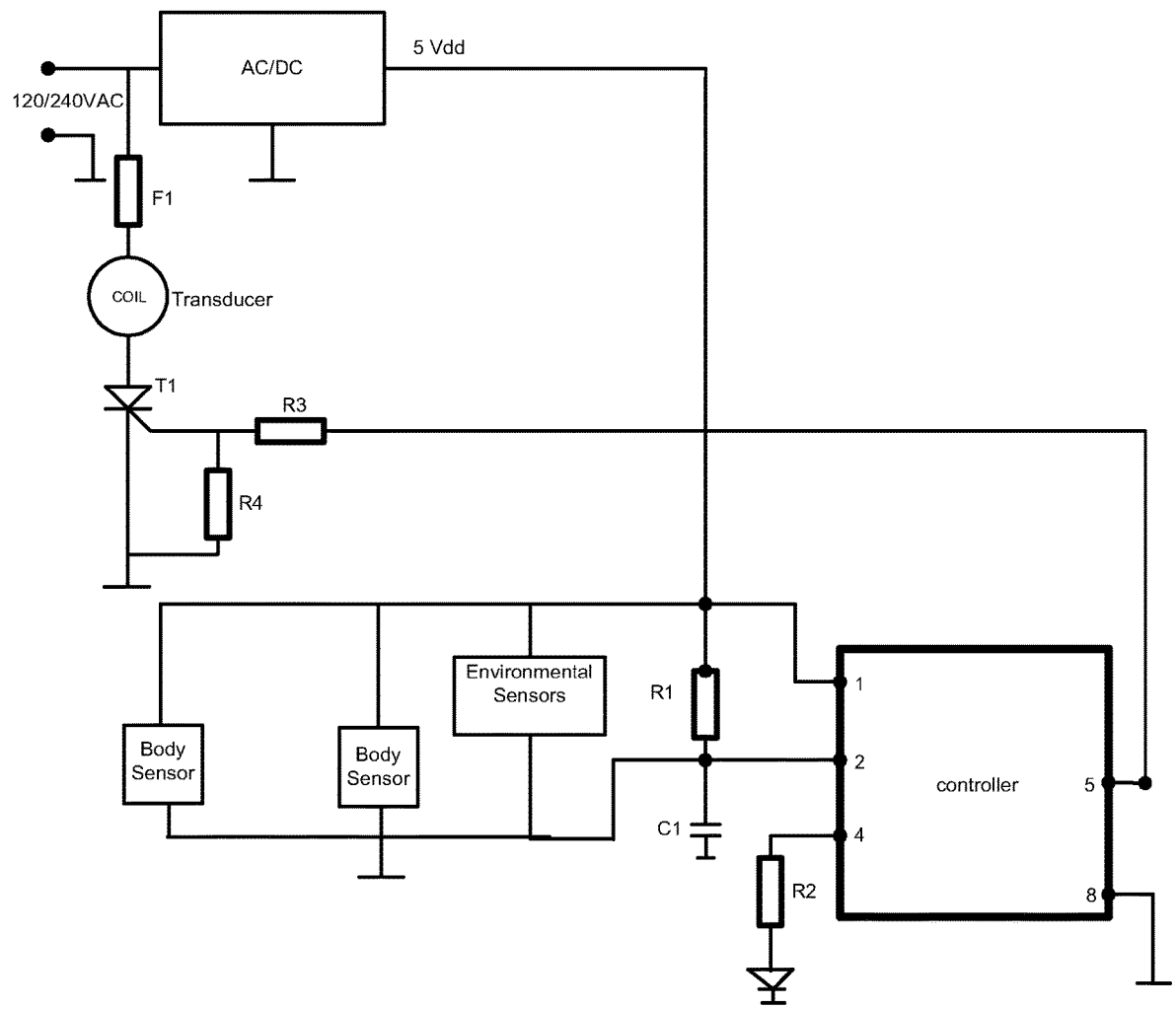
FIG. 7 is an electrical schematic of yet another embodiment of the disclosed apparatus.

FIG. 7 shows a general basic interconnection of environmental and body sensor connected to a microcontroller (non-limiting ex.PIC 12F629). The output of the microcontroller opens the gate of TRIAC T1, producing magnetic force in connection with any 120/240 V ac.

Figure 8:
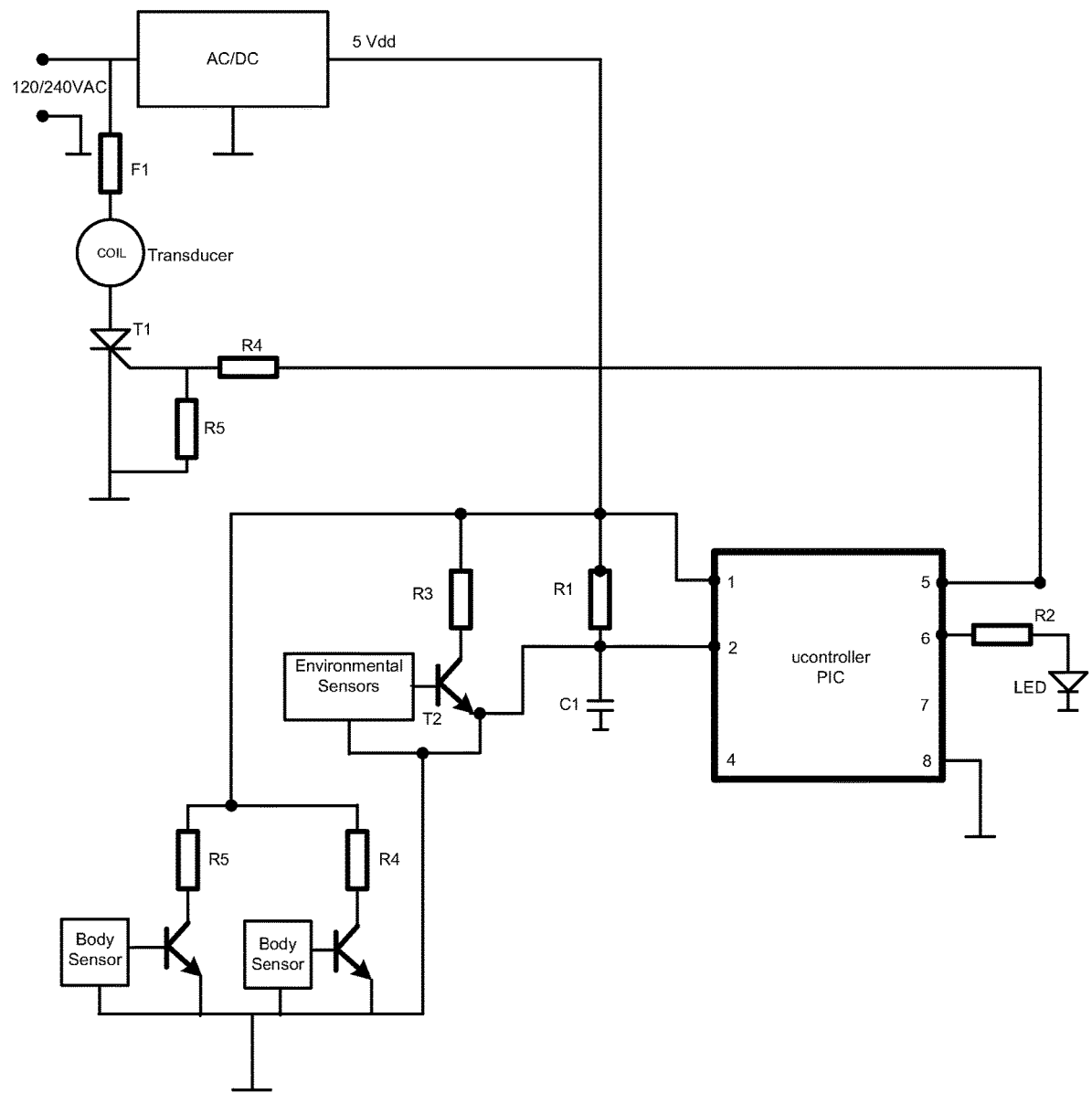
FIG. 8 is an electrical schematic of even still another embodiment of the disclosed apparatus.

In FIG. 8 the magnetic pulse generator uses a microcontroller having a clock frequency set by an external RC. The output frequency can be adjusted by resistor R1. Resistor R1 can be connected in parallel with one or more resistors (R3, R4, and R5) based on the state of the associated sensors. The pulses generated can be equal in length and can open TRIAC T1 allowing the coil to be energized by the AC voltage.

Figure 9:
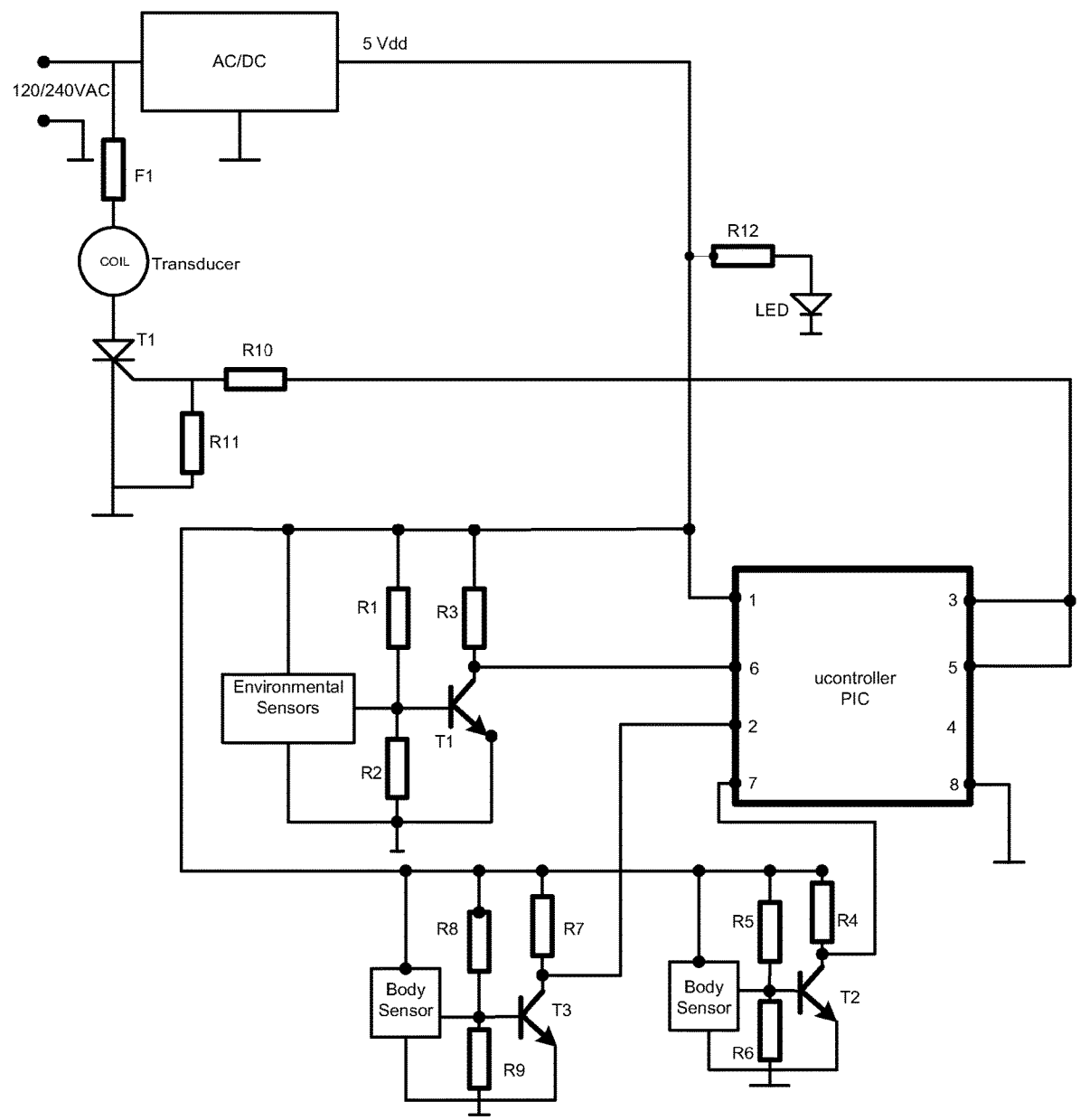
FIG. 9 is an electrical schematic of still further another embodiment of the disclosed apparatus.

In FIG. 9 environmental and body sensor's sensitivity can be adjusted by programming a comparator threshold level in the controller software. Each sensor can produce an electric signal in response to a designated environmental or body purpose (ex. temperature, humidity, heartbeat, pH. etc.). Transistors T2, T3, T4 can be provided to amplify the signals and allows adjustments of the circuit sensitivity by altering the bios voltage of transistors (T2, T3, T4). A short electric pulse from the output of the microcontroller can be sufficient to open the gate of T1 and energize the coil through the alternating voltage.

Figure 10:
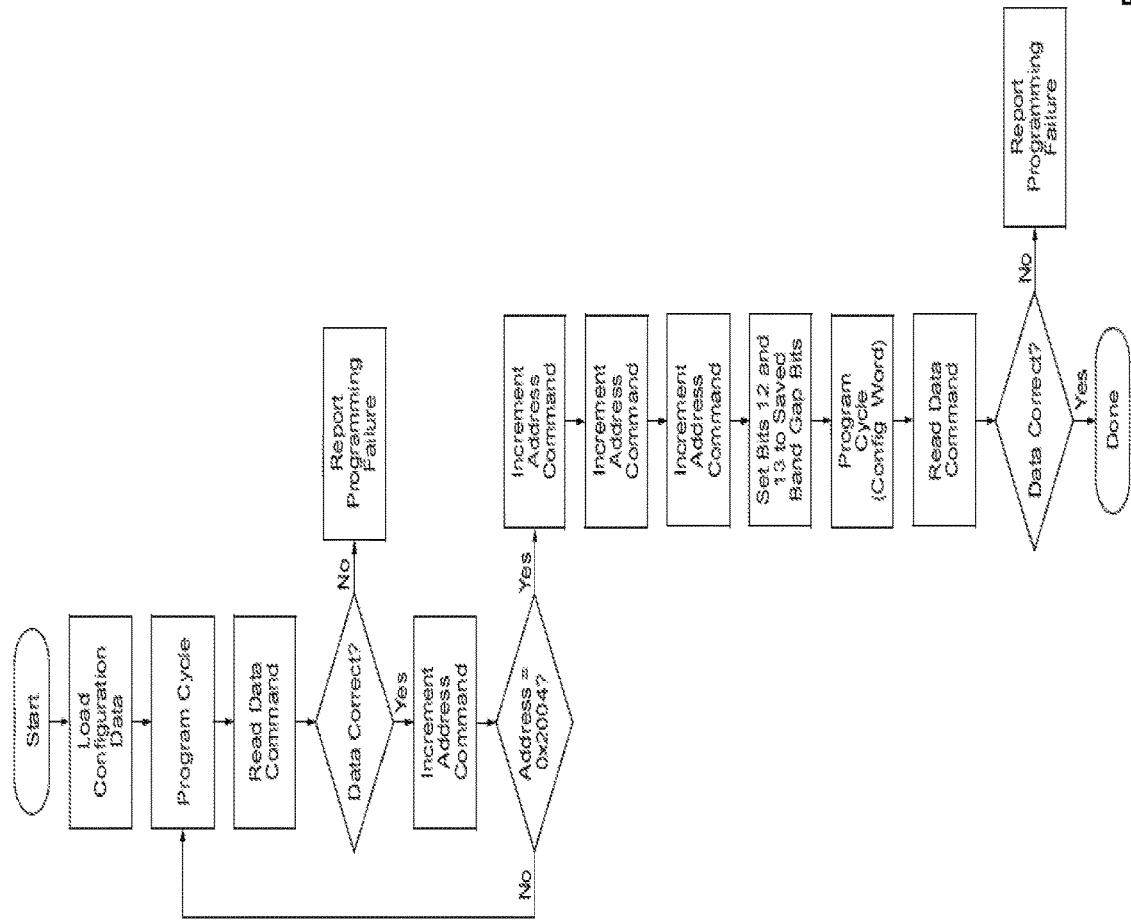
FIG. 10, FIG. 11 and FIG. 12 are flowcharts for the memory configuration, data memory and memory program for the disclosed apparatus.
Figure 11:
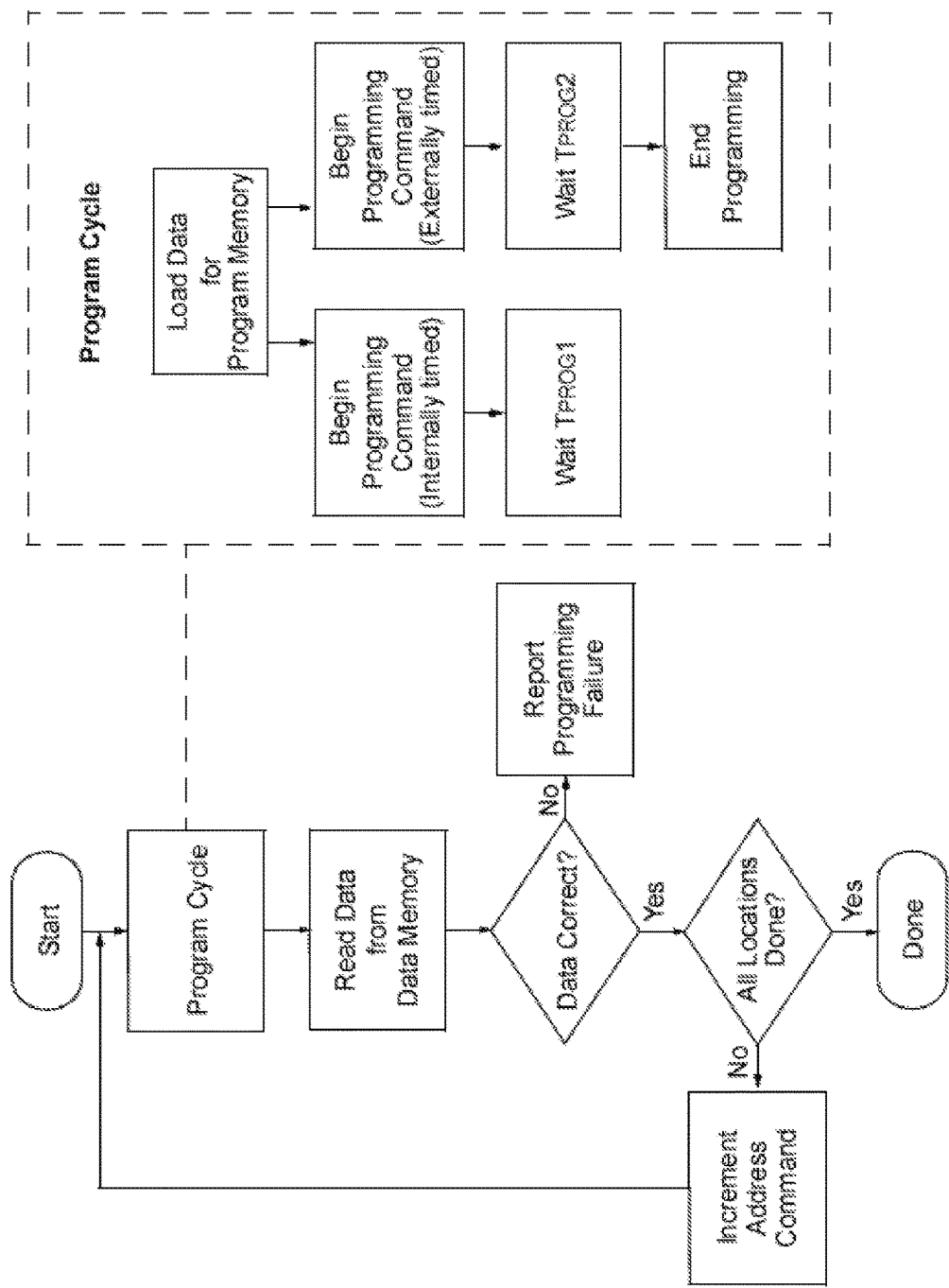
Figure 12:
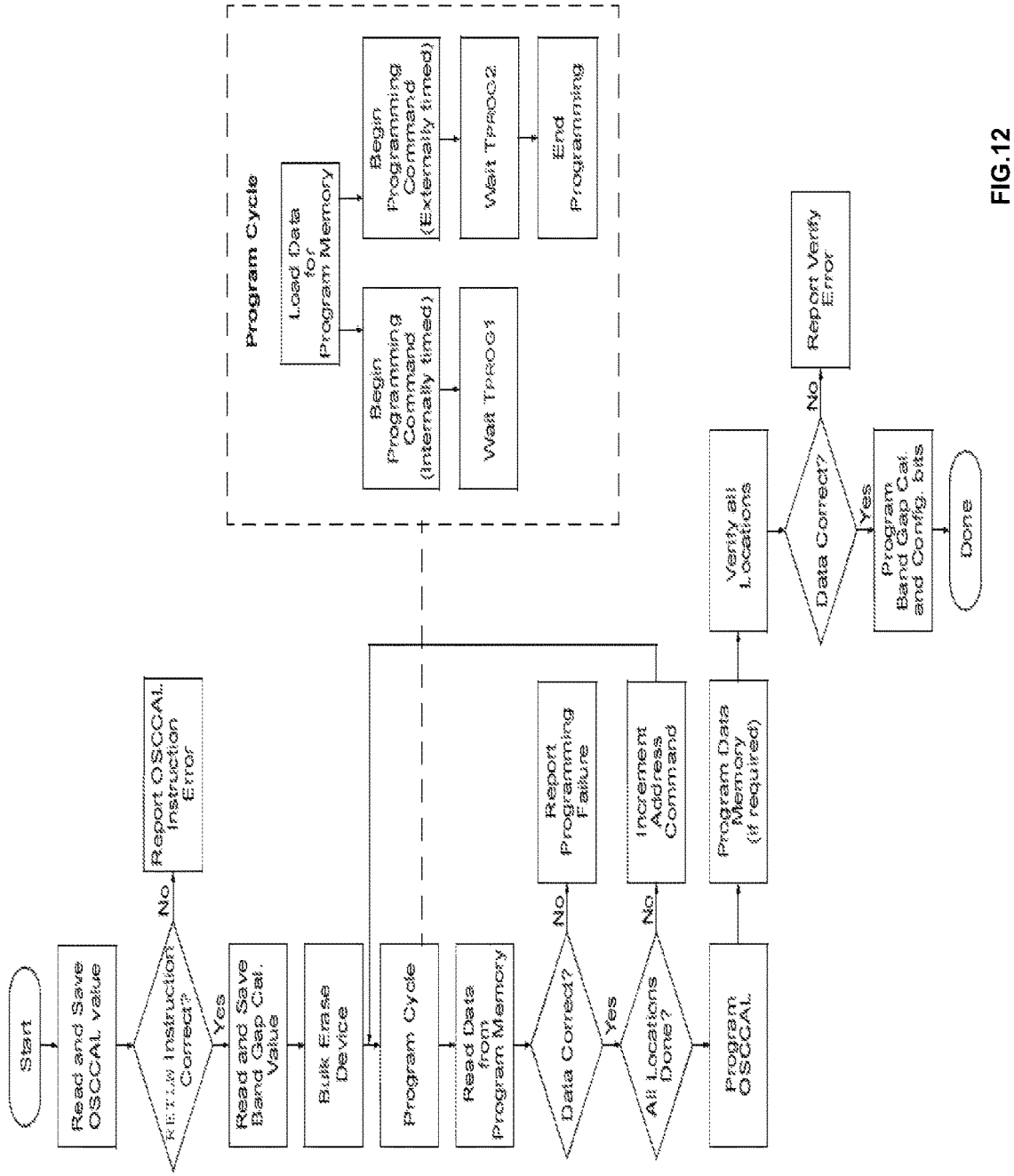

FIG. 10, FIG. 11 and FIG. 12 illustrate the steps and decisions performed in connection with the memory configuration; data memory and memory program, respectively, for the apparatus.

The disclosed apparatus can provide for a magnetic pulse generator, with low frequency using an IC chip or controller to open a gate, whose opening allows high voltage (AC) to energize the transducer (coil) for specific period of time. Preferably, the frequency can be programmed to range anywhere from about 1 Hz to about 170 Hz, though such range is not considered limiting.

In summary, the disclosure provides for a method and apparatus for regenerating and healing a live human or animal body. The apparatus can be comprised of at least one sensor (environmental sensor and/or body sensor); an electrical circuit generating ultra-low frequency DC waves with varying (about 1 to about 30 Hz) based on information received from the sensor(s), and a transducer or electromagnetic resonator creating an electromagnetic force based on the output of the electrical circuit, by opening the gate of a TRIAC, semiconductor device or other electronic device at ultra-low frequency, allowing low frequency AC current to energize the transducer and thus providing for a novel and effective way to rejuvenate (regenerate, heal, balance) live human and animal bodies. The above described apparatus and method can preferably also be comprised with at least one varying component influenced by the information received from the sensor(s); and can produce a low frequency from about 1 Hz to about 30 Hz, preferably provided in a square wave form and can have an electromagnetic force intensity from about 0.001 Gauss to about 0.45 Gauss.

Preferably, the gate (from a TRIAC, other semiconductor device or other electronic device with the equivalent of a gate) can be opened/enabled at an ultra-low frequency provided by the electrical circuit varying the frequency and the duty cycles. With the gate enabled, on the positive side of the duty cycles (which can vary with the frequency based on information from the sensor(s) the transducer can be energized with sinusoidal wave, low frequency AC current from an AC power supply.

The transducer can be energized with short AC sinusoidal waves low frequency (preferably about 47 to about 65 Hz) current (which preferably never start and stop at same phase or point) only on the positive side of duty cycles generated by the ultra-low frequency from the electric circuit, varying the ultra-low frequency, and duty cycle based on information from at least one environmental and/or body sensor. In order to closely replicate earth's magnetic pulse, the AC sinusoidal wave forms preferably do not all start and stop at the same phase or point such that there is no repeating pattern for the starting and stopping phase point.

The body and environmental sensors could be an integral of the device and function as describe above, or the sensors can be separate from the device and communicate with the device using known and future developed wireless communication protocols without changing the functionality described.

In the wireless configuration, the sensors can be a separate module which communicates wirelessly with the main device. Alternatively, the sensors can be existing sensors, such as those provided using an app on an electronic device, such as, but not limited to, a smart phone, cell phone or tablet. In either wireless embodiment, the sensors can communicate with the main device in order to change the variables as describe above. Non-limiting examples of sensor information that can be obtained using software apps for an electronic device include, but are not limited to, heartbeat, body temperature, blood sugar level, etc. The information obtained can be wirelessly sent to the main device and have same functionality and results, benefits, etc. similar to the sensors that are provided as an integral part of the device.

The above described parts can be provided within a housing. Where the sensors are integral, the at least one environmental and/or body sensor, the TRIAC (or other semiconductor or electrical device), the electrical circuit and the transducer or electromagnetic resonator can be contained within the housing. In the above described wireless configuration, the sensors would not be contained within the housing. Additionally, an electrical plug having at least two prongs can extend out of the housing, with the plug connecting the apparatus with a source of high voltage AC when the at least two prongs are inserted within a live electrical socket outlet.

Figure 13:
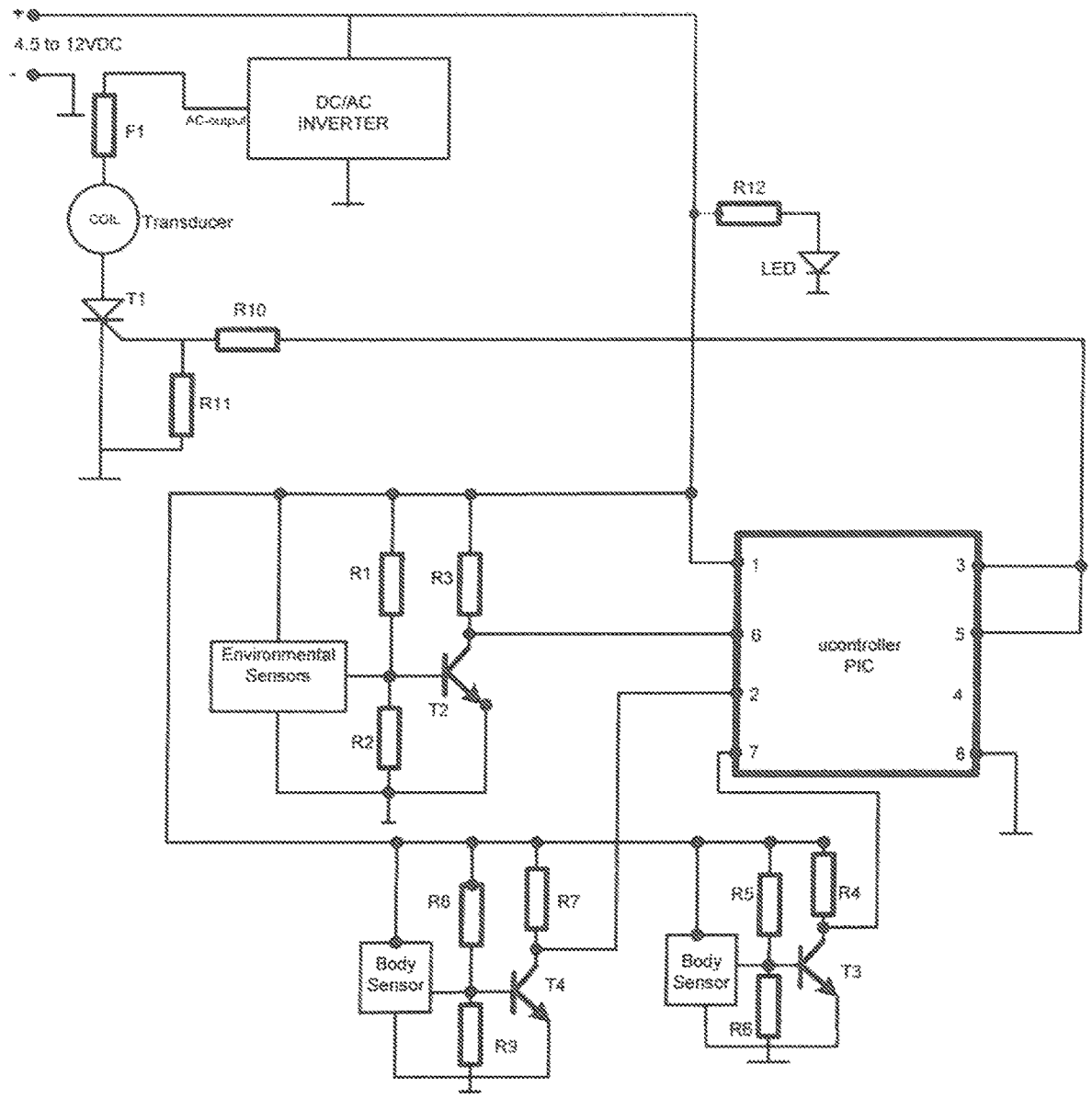
FIG. 13 is an electric schematic for another embodiment of the disclosed apparatus, which can be powered by a DC source of energy (one or more batteries or rechargeable batteries) in accordance with the present disclosure.
Figure 15:
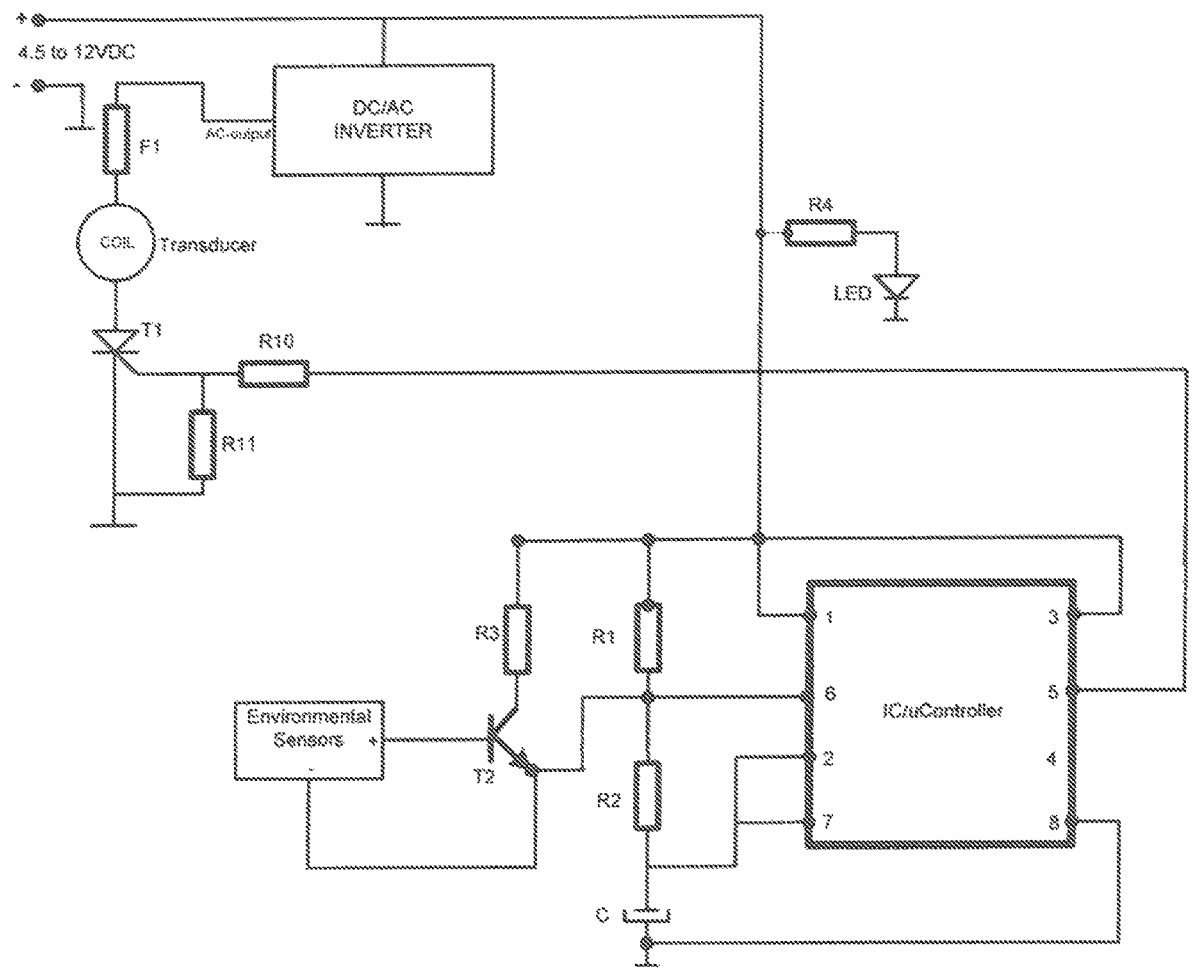
FIG. 15 is an electric schematic for still another embodiment of the disclosed apparatus preferably using a DC source of energy.

FIG. 13 illustrates another embodiment this time where a power source can be provided such as one or more batteries or rechargeable batteries in lieu plugging the apparatus into an AC outlet to allow the apparatus to be mobile. The apparatus shown in FIG. 13 preferably uses at least one environmental sensor and at least one body sensor to provide information to the microcontroller. The microcontroller sends an output signal to open a gate T1 to allow a coil to be energized by AC voltage circuit, preferably created by a DC/AC inverter, to generate a magnetic pulse field FIG. 15 illustrates another embodiment again where a power source can be provided such as one or more batteries or rechargeable batteries, or another DC power source. The apparatus preferably uses at least one environmental sensor which provides information to the microcontroller. The microcontroller or IC sends an output signal to open the gate T1 which allows the coil to be energized by AC voltage circuit created by the DC/AC inverter, to generate a magnetic pulse field.

The apparatus disclosed in FIG. 15 preferably presents one or more environmental sensors that provides the information that can be used to control and determine the cycles for producing magnetic energy, in connection with alternative current created by the provided DC/AC inverter, using a DC source of power.

As seen in the schematic of FIG. 15, a circuit DC/AC inverter provides the alternative current output for energizing the resonator. The output of the IC or microcontroller can generate a train of square wave pulses determined by the information it receives from the environmental sensors and the signal/output from the IC or microcontroller can be preferably provided or applied to the gate of T1 (transistor or triac). Based on the information received from the environmental sensors, the signal cycles sent to the gate of T1 allow for alternate or alternative (AC) voltage to transfer or pass through the transducer to produce the pulsed magnetic energy.

Figure 14:
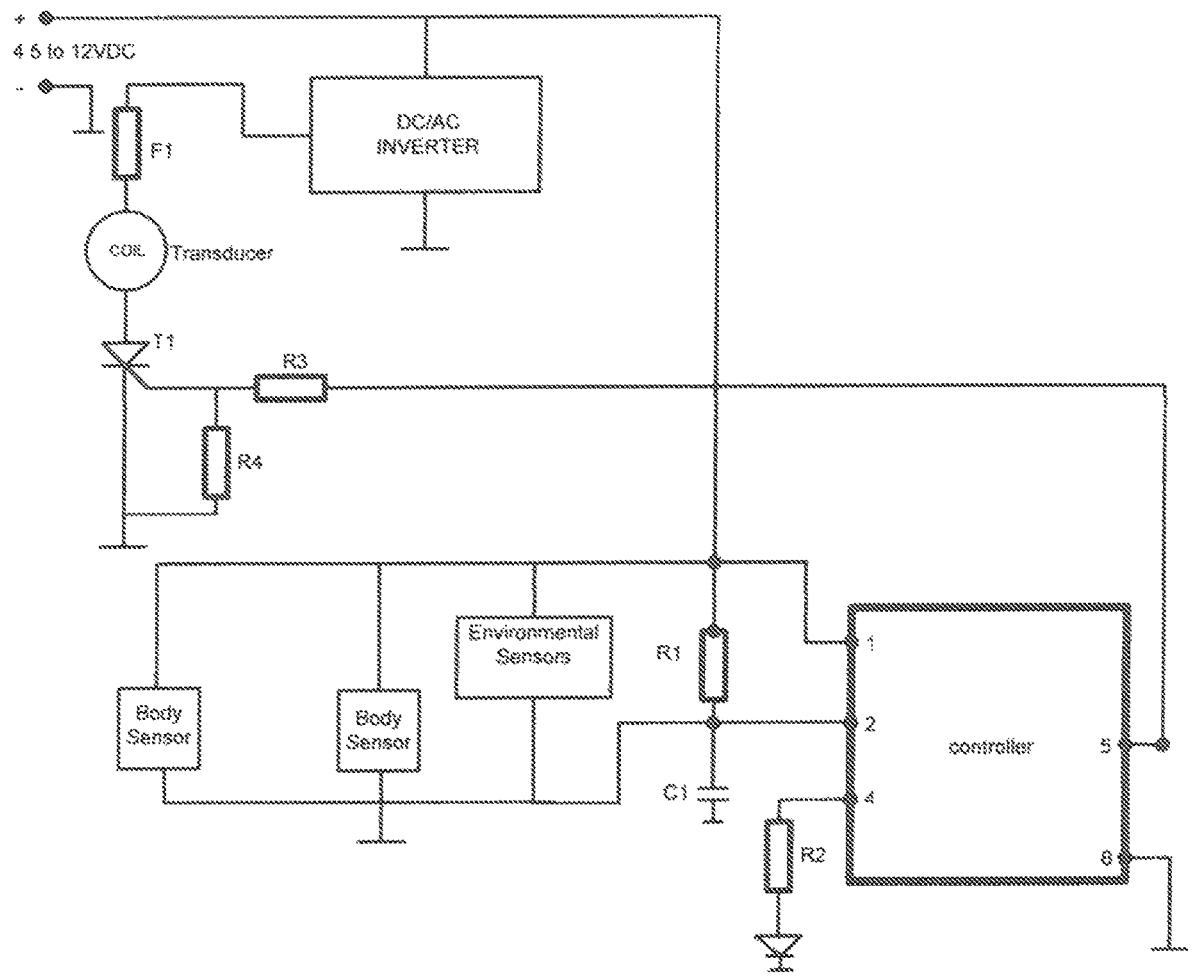
FIG. 14 is an electrical schematic of yet another embodiment of the disclosed apparatus preferably using battery power.

The embodiments shown and described in FIG. 13, FIG. 14 and FIG. 15 can preferably use DC power, which allows the apparatus to be a portable embodiment. The batteries voltage can be in 4.5 to 12 volts range, but such range and voltage values are not considered limiting.

The output from the DC/AC inverter does not necessary need to be a high voltage AC, just AC voltage, of any level (low, mid or high) can be used. Though not considered limiting, the AC output can be in 4 to 220 VAC range with a frequency preferably between about 47 to about 150 Hz. All values are provided as examples and are not considered limiting.

Additionally, the disclose apparatus (various embodiments) can be used with an electronic device, such as, but not limited to, an APPLE watch or FITBIT technology, to monitor a person's vitals, such as by announcing when your body needs to be in the proximity of disclosed apparatus (based on range proximity) or to signal or instruct the disclosed apparatus to increase/decrease frequency. Monitoring vitals can increase body efficiency and may reduce overall pain.

Figure 16:
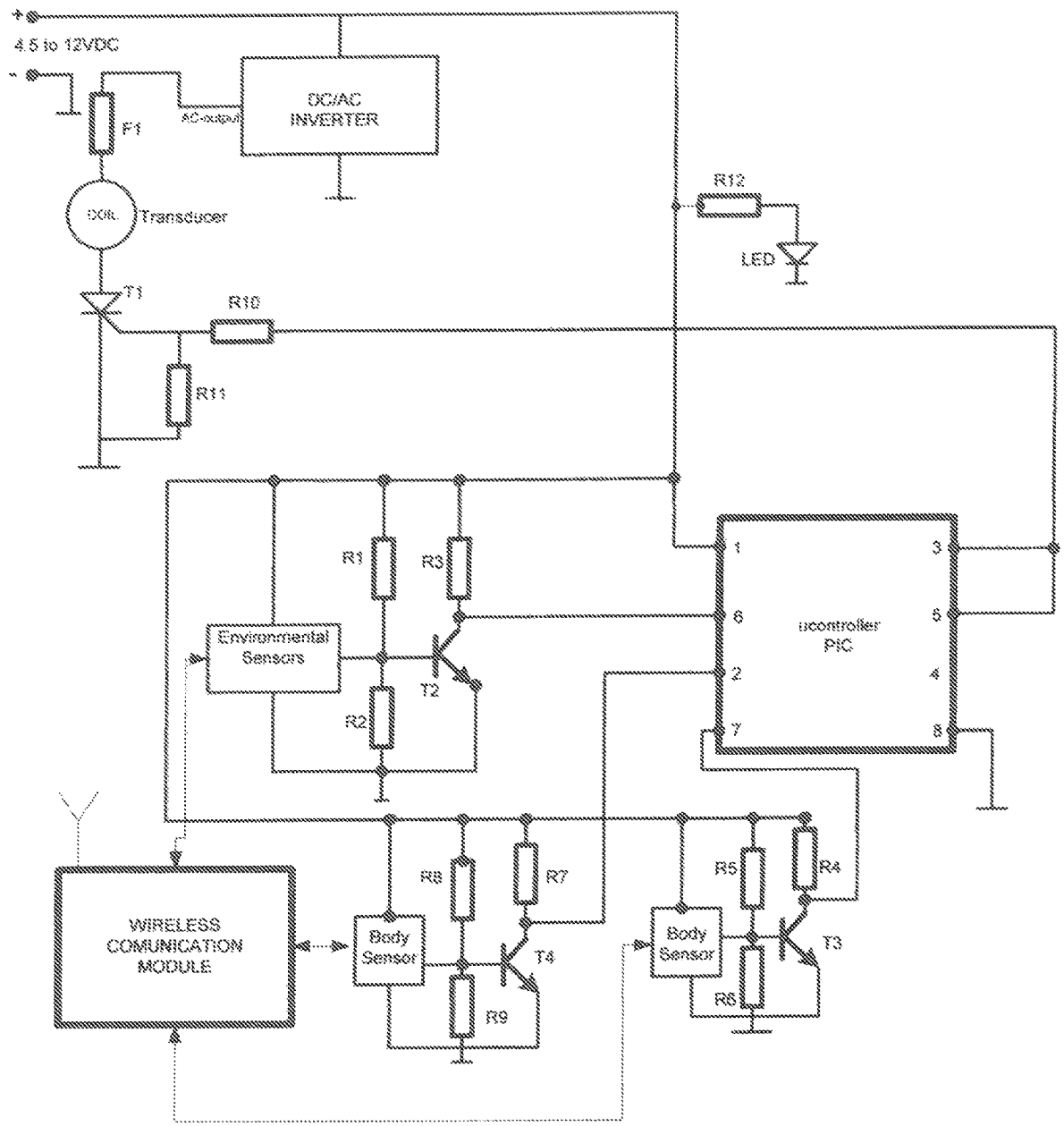
FIG. 16 illustrate an electric schematic for another embodiment of the disclosed apparatus preferably provided with wireless communication capabilities.

FIG. 16 illustrates another embodiment of the disclosure which can add or provide a communication module preferably using Wi-Fi data, Bluetooth or cellphone data to communicate with a cellphone, tablet, pc or any portable device with an operating system (OS system) preferably used to vary frequency and/or intensity of magnetic field based on the body vitals information received from the sensors. In this embodiment, the apparatus preferably can have or be provided with a communication module using Wi-Fi data, Bluetooth or cellphone data to communicate with a cellphone, tablet, pc or any portable device with an OS system, for varying frequency or intensity of magnetic field based on body vitals sensors.

The body and environmental sensors can be integral of or internal within the device and function as describe above, or the sensors can be separate from the device and communicate with the device using known and future developed wireless communication protocols without changing the functionality described.

The apparatus disclosed in FIG. 16 can be provided with a communication module using Wi-Fi data, Bluetooth or cellphone data to communicate with a cellphone, tablet, pc or any portable electronic device with an OS system, for varying frequency or intensity of magnetic field based on body vitals sensors, and all are considered within the scope of the disclosure.

In the wireless configurations, the sensors can be a separate module which communicates wirelessly with the main device. Alternatively, the sensors can be existing sensors, such as those provided using an App on an electronic device, such as, but not limited to, a smart phone, cell phone, tablet or similar electronic devices. In the wireless embodiments, the sensors can communicate with the main device in order to change the variables as describe above. Examples of sensor information that can be obtained using one or more software apps for an electronic device include, but are not limited to, heartbeat, body temperature, blood sugar level, pulse rate, blood pressure, etc. The information obtained can be wirelessly sent to the main device and can have the same functionality and results, benefits, etc. similar to the sensors that are provided as an integral part of the device.

In all embodiments, the apparatus can preferably automatically and continuously, on its own, vary simultaneously both the electromagnetic energy and the frequency and can alternative the polarity based on environmental information the IC/microcontroller receives from the one or more environmental sensors and/or based on body/body vital information the IC/microcontroller receives from the one or more body sensors.

For the non-portable/non-mobile embodiments, when the device/apparatus is connected to an AC outlet it can be "on" and working continuously, and the device does not need to have an on/off switch for turning the device off/on, though it is within the scope of the disclosure to include such switch to the circuit. Thus, the device can be preferably continuously on and thus continuously and automatically feeding information from the sensor(s) to the microcontroller. Upon receiving information from the sensor(s), a microcontroller preferably automatically processes the information and changes and automatically makes any adjustments needed on its own and without any input by a human user. Thus, for the AC/non-portable embodiments the device can automatically and continuously vary the frequency, magnetic polarity and intensity on its own.

Figure 17:
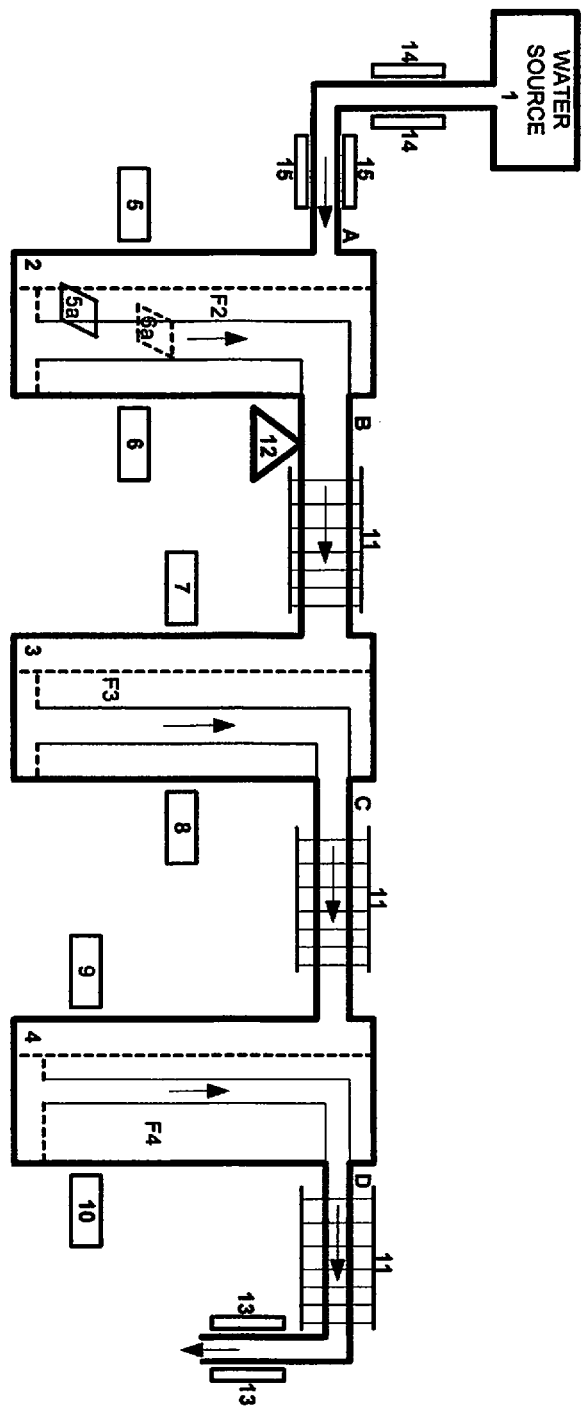
FIG. 17 illustrates a block diagram of the apparatus and method used for exposing water to low or ultra-low frequency electromagnetic fields through transversal or perpendicular and longitudinal or parallel magnetization of water with preferably three stages of water filtration and static magnetization in accordance with the disclosed apparatus and method.

FIG. 17 shows an embodiment where one or more of the above described energy generating apparatuses can be used as part of a system and method for exposing water to low or ultra-low frequency electromagnetic fields through transversal (perpendicular) and longitudinal (parallel) magnetization of water with preferably three stages of water filtration and static magnetization.

Block 1 represents a source of water which can be collected rain water, tap water, sea water, water made from air humidity, etc. and all sources of water are considered within the scope of the disclosure. If the water source is from rain or air humidity, distillate water, the first stage (F2) can be directing the water through a natural minerals filter, with the purpose of adding one or more minerals (e.g. calcium, potassium, manganese, magnesium etc.) to the water. A sensor 12 can be preferably provided after the first stage for determining the levels of matter in the water, such as, but not limited to, minerals, lead, etc. Information from sensor 12 is fed back to a microprocessor, server or other computer or computing device (collectively "microprocessor") for processing the information received from sensor 12. What for the water traveling through the first stage is used for (e.g. hydration, lab experiment, etc.) can determine the amount or level of matter in the water, such as, but not limited to, the amount of minerals. For example, for hydration uses a higher level of minerals in the water may be preferred, whereas for certain lab experiments a lower level or nil amount of minerals in the water may be desired. The electromagnetic field created for the first stage will have an affect on the level of minerals in the water. Where no or a low of amount of minerals are wanted, after automatically receiving data or information from sensor 12, the microprocessor can automatically determine if the level of minerals in the water is too high and, if so, can automatically adjust the device creating the electromagnetic field for first stage F2 to raise or increase the intensity of the electromagnetic field so as to lower the mineral level of subsequent water traveling out of first stage F2. As another non-limiting example, where the water is used for drinking water, if the data or information received by the microprocessor from sensor 12, reveals a low level or not enough of minerals in the water, the microprocessor can automatically adjust the device creating the electromagnetic field for first stage F2 to lower or decrease the intensity of the electromagnetic field so as to raise the mineral level of subsequent water traveling out of first stage F2. Sensor 12 can also be placed before the first stage to determine the mineral level prior to the water reaching first stage F2 and similarly make adjustments to the intensity level of the electromagnetic field from sensor readings at this point. Additionally, it is also within the scope of the disclosure, to have sensors 12 placed at the beginning of first stage F2 and at the end of first stage F2. In one non-limiting embodiment, sensor 12 can be a total dissolved solids ("TDS") sensor/reader 12 and provides information for the source of water traveling through the first stage that is used by the microprocessor for increasing or decreasing the hydration properties by adjusting the intensity level for the electromagnetic field used for first stage F2.

Increasing magnetic or electromagnetic field helps to dissolve the minerals in the water. Increasing such field helps to reduce the amount of minerals in the water, which can be particularly beneficial for non-hydration uses for the source of water.

Where the water source is tap water the necessity of using natural mineral filter can be determined by the readings from sensor 12, which in certain embodiments can be a TDS sensor. Where the levels of the water are known to be satisfactory and not needing any adjustments or maintenance, a bypass fluid line can be provided in the water flow line such that the source of water can bypass going through first stage F2. Opening a valve in the line to divert the source of fluid through the bypass line can be manually performed or controlled by a signal sent from the microprocessor.

Between the water source and a first stage and after a last electromagnetic pulse at the water exit one or more permanent magnets 13, 14 and 15 can be provided and in a preferred embodiment can be relatively strong neodymium rare-earth magnets and create a longitudinal static magnetic field to create virtual electric current in the water while the water is moving.

Blocks 2, 3 and 4 in FIG. 17 represent the preferred are three stages of transversal (perpendicular) pulse magnetization based on the flow of the water. Some or all of these blocks can be provided with a roll of filtration or some other filter element(s).

Pulse magnetization longitudinal (parallel) with the water flow can be provided by the magnetic resonators or transducers 11, such as, but not limited to, the magnetic resonators or transducers described herein in FIGS. 1 through 16. Components 5, 5a, 6, 6a, 7, 8, 9 and 10, whose function and use are described below can also be magnetic resonators or transducers, such as, but not limited to, the magnetic resonators or transducers described herein in FIGS. 1 through 16.

Taking in consideration the natural cycle of water (i.e. first comes with pressure, potential energy, splashing on rocks, goes underneath rocks and earth and experiences pressure again, obtains minerals from the ground, cleaned from contact coral, sponges, etc.) the disclosed system can be designed/programmed to mimic such natural cycle.

As one non-limiting flow example, the water coming from source 1 can go through tube/conduit/pipe A to first stage 2, where the water can be preferably perpendicularly magnetized by electromagnets 5, 6, 5a and 6a. Based on the Lorentz force, forces will induce an electric current on the water. Most colloids of biological origin are negatively charged and attract a shell of positively charged ions, with di or multivalent ions dominating because of their extra charge. With the system directing the water containing these particles through a magnetic field, the Lorentz forces drive the negative particles and their oppositely charged ionic shells in opposite direction. This same process can be repeated for stages two and three (Block 3 and Block 4, respectively). The perpendicular electromagnetic force can be generated by a four axis resonate frequency member preferably composed of four conductive transducers/resonators/coils placed on each side of the enclosures for each of the stages. This electromagnetic resonant assembly preferably comprises four conductive transducers/resonators/coils 5, 6, 5a and 6a connected sequentially to the microcontroller output, with two sequentially in opposite axis at the same time (affecting the water transversal or longitudinal) or all four simultaneously pushing the magnetic fields (affecting the water both transversal and longitudinal at the same time).

Other number of conductive transducers/resonators/coils can also be provided and similarly connected with the microcontroller and are also considered within the scope of the invention. Individuals apparatuses 5, 6, 5a and 6a can be arranged in four axes as seen in FIG. 17. After the first perpendicular magnetization, the water leaves the first stage through tube/pipe/conduit B, where it can be magnetized again by electromagnets 11, but in parallel with the water flow 11. The water can be subjected to the same process of parallel magnetizations after leaving stages two and three through tubes/conduits/pipes C and D also by electromagnets 11. The water will flow from the source to end point of the system throw tubes A; B; C; D (FIG. 17) and all of them have different dimensions. Alternating the diameters we can create a Brownian movement of water molecules and simultaneous increase the pressure inside the system.

Differing pressures within the system can be used and achieved by one or more different mechanisms, including, without limitation, having different inner diameter sizes for the conduits (See conduit A, B, C and D in FIG. 17) and/or differing pore sizes (i.e. differing microns) for the filters contained within the stages. The differing pressure can help with producing more Brownian movement for the water molecules.

Depending on how the magnetic resonators or transducers are secured or positioned in the system will determine whether they provide perpendicular magnetizing/electromagnetizing or parallel magnetizing/electromagnetizing. For example, magnetic resonators or transducers can be wrapped around the conduit to create a parallel effect for the magnetic field.

Additional transducers/resonators/coils can also be provided at the beginning and end of the system, along with the permanent magnets.

Perpendicular orientation for the magnetic field may help to clean the water from bacteria and other matter, which the parallel magnetic field may dissolve or reduce the particles or total solids in the water. The various magnetizing and magnetic fields may also aid in changing the structure of the water.

The filters F2, F3 and F4 which can be used in the preferred several stages can be used for to increasing the pressure of the water flow and can create a Brownian movement or pedesis of the water molecules. The connection tubes B and C between the stages can have the same inner diameter though such is not considered limiting.

In addition to a TDS sensor, sensor 12 can also be a temperature sensor whose data can be used by the microprocessor to send a signal to alternate the frequency and intensity of the magnetic field, similar to as how describe in U.S. Pat. No. 9,724,535, which is incorporated by reference in its entirety. Though not considered limiting, the electromagnetic fields used for the system of FIG. 17 can be produced by apparatuses and devices described in U.S. Pat. No. 9,724,535 and shown and described herein in FIG. 1 through 16. Further embodiments for sensor 12 can be: photo sensor, barometric sensor and/or ORP (oxidant reduction potential) sensors. The sensors send information to microprocessor (IC) for processing and determining how much, if any, varying of the frequency and electromagnetic intensity is needed.

In a liquid state, in spite of 80% of electrons in H2O being concerned with bonding, three of the atoms do not stay together as the hydrogen atoms are constantly exchanging between water molecules. Liquid water is affected by magnetic fields and such fields can assist in the purification of the water.

Exposure to lower magnetic fields have been shown, in simulations, to increase the number of monomer water molecules but, rather surprisingly the tetrahedral (which is the most common arrangement of hydrogen atoms around an oxygen with two hydrogen atoms covalently bonded to oxygen and two attached by hydrogen bonds) at the same time. Other studies show an increase in cluster size in liquid water caused by exposure to magnetic fields. Weak magnetic fields along (parallel) and perpendicular magnetic fields have also been shown to increase the evaporation rate for the water, similar to rainwater evaporation from splashing against rocks and other items on the earth's surface when falling from the sky.

These effects are consistent with magnetic fields weakening the Van Der Walls bonding between the water molecules and the water molecules being more tightly bound, due to the magnetic field reducing the thermal motion of the inherent charges by generating dampening forces. Magnetic fields can also increase proton spin relaxation which may speed up same reactions dependent on proton transfer. Preferably stages 2 and 3 can be used for these affects (i.e. create pressure in the water, prepping the water, etc.), while stage 1 is used for filtering the water (i.e. eliminating or reducing bacteria, removing or reducing relatively big particles from the water, etc.). The frequency used for the electromagnetic resonators/transducers preferably between 8 and 12 Hz.

Electromagnetic fields that attempt to reorient the water molecules should necessitate the breakage of same hydrogen bonds.

The solubility properties of the water will change in presence of such fields and result in the concentration of dissolved gases and hydrophobic molecules at surfaces followed by reaction or phase changes (Nano bubbles). It is also possible that these processes may result in the production of low concentrations of hydrogen peroxide in a similar manner to mechanical vibration. Such changes can clearly result in effects lasting for a considerable time, giving rise to claims for memory effects.

In addition to breakage of hydrogen bonds, electromagnetic fields may perturb in the gas/liquid interface and produce reactive oxygen. Change in hydrogen bonding may affect carbon dioxide hydration resulting in pH changing. Thus, through use of the disclosed system and method, ultra-low frequency electromagnetic fields can have significant and lasting effects on liquid water.

The result of the structured water through being subject to the disclosed apparatus and method is that the water has more energy while offering increased hydration for people, animals, plants and things. The natural action of water tumbling over rocks, down waterfalls, flowing through twists and turns as it actively descends a mountain actually structures the water. Through these natural processes, the molecular structure of water can be changed to reflect less surface tension, neutralize toxins, clear memory and balance on a particle level. Water molecules are free to move and in an energetically alive, fresh and vibrant manner. The disclosed novel system/apparatus and method are designed to create a similar "structuring" effect on the water flowing through the system/apparatus.

All measurements, amounts, frequencies, voltages, intensity amounts, sizes, shapes, percentages, configurations, securement or attachment mechanisms, dimensions, filtration mechanisms, sealing members, numbers, ranges, part locations, values, percentages, magnet types, materials, orientations, methods of manufacture, etc. discussed above or shown in the drawing figures are merely by way of example and are not considered limiting and other measurements, amounts, frequencies, voltages, intensity amounts, sizes, shapes, percentages, configurations, securement or attachment mechanisms, dimensions, filtration mechanisms, sealing members, numbers, ranges, part locations, values, percentages, magnet types, materials, orientations, methods of manufacture, etc. can be chosen and used and all are considered within the scope of the disclosure.

Furthermore, one or more features, components, characteristics, sensors, etc. discussed for one embodiment of the disclosure can also be used with another of the above discussed embodiments of the disclosure.

The term "conduit" shall broadly include conduits, tubing, pipes and any other device that fluid/water can flow through. The term "housing" can be considered a separate structure having a conduit therein serving as the internal water path or the conduit can also be considered a housing. The use of "transducer" shall broadly include transducers, magnetic resonators, electromagnetic resonators, resonators, coils and any other device capable of creating the desired magnetic field or pulsed magnetic field. The term "conditioning" shall broadly include various affects on the source of water such as, but not limited to, cleaning, removing bacteria, removing particles, removing dirt, removing waste, removing hazardous materials, removing hazardous chemicals, adding minerals, adding vitamins, adding antioxidants, adding other supplements, etc.

Additionally, for any numerical ranges discussed above, any combination of numbers within the range can be used to create a smaller size range from the outer limits of the numerical range specified and all such smaller ranges are also considered to be within the scope of the disclosure and also incorporated by reference without particularly listing each specific numerical value for the smaller ranges.

Unless feature(s), part(s), component(s), characteristic(s) or function(s) described in the specification or shown in the drawings for a claim element, claim step or claim term specifically appear in the claim with the claim element, claim step or claim term, then the inventor does not considered such feature(s), part(s), component(s), characteristic(s) or function(s) to be included for the claim element, claim step or claim term in the claim for examination purposes and when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the disclosed apparatus and method have been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. An apparatus for structuring water, comprising:
   a first stage for conditioning water flowing therein from a source of water through transversal/perpendicular pulse magnetization, the first stage having a first housing defining a first internal water path therein, the first internal water path having a first end and a second end;
   a first conduit having a first end and a second end, the first conduit in fluid communication with the source of water and in fluid communication with the first internal water path;
   a second stage for conditioning the water through transversal/perpendicular pulse magnetization, the second stage having a second housing defining a second internal water path therein, the second internal water path having a first end and a second end;
   a second conduit having a first end and a second end, the second conduit in fluid communication with the first internal water path at a first end of the second conduit and in fluid communication with the second internal water path at the second end of the second conduit;
   a third conduit having a first end and a second end, the third conduit receiving the water flowing out of the second end of the second internal water path;
   at least one permanent magnet associated with the first conduit for creating a first static a magnetic field that is applied to the water when the water is traveling through first conduit to create virtual electric current in the water while the water is moving;
   a first plurality of electromagnetic transducers positioned with respect to the first housing to create a first transversal pulse magnetic field that is applied to the water when the water is traveling through the first internal water path within the first housing;
   a first electromagnetic transducer positioned with respect to the second conduit to create a first longitudinal pulse magnetic field that is applied to the water when the water is traveling through the second conduit;
   a second plurality of electromagnetic transducers positioned with respect to the second housing to create a second transversal pulse magnetic field that is applied to the water when the water is traveling through the second internal water path within the second housing; and
   a second electromagnetic transducer positioned with respect to the third conduit to create a second longitudinal pulse magnetic field that is applied to the water when the water is traveling through the third conduit;
   wherein the water is subjected to simultaneous transversal and longitudinal pulse magnetic fields during the first stage of conditioning from perpendicular magnetizing created by a four axis resonate frequency member comprising the first plurality of electromagnetic transducers with two axis of the four axis sequentially in opposite axis at a same time;
   wherein the water is subjected to simultaneous transversal and longitudinal pulse magnetic fields during the second stage of conditioning from perpendicular magnetizing created by a four axis resonate frequency member comprising the second plurality of electromagnetic transducers with two axis of the four axis sequentially in opposite axis at a same time.

2. The apparatus for structuring water of claim 1 further comprising:

a third stage for conditioning the water through transversal/perpendicular pulse magnetization, the third stage having a third housing defining a third internal water path therein, the third internal water path having a first end and a second end;

a fourth conduit having a first end and a second end, the fourth conduit in fluid communication with the second internal water path at a first end of the fourth conduit and in fluid communication with the third internal water path at a second end of the fourth conduit;

a third plurality of electromagnetic transducers positioned with respect to the third housing to create a third transversal pulse magnetic field that is applied to the water when the water is traveling through the third internal water path within the third housing;

a third electromagnetic transducer positioned with respect to the fourth conduit to create a third longitudinal pulse magnetic field that is applied to the water when the water is traveling through the fourth conduit wherein the water is subjected to simultaneous transversal and longitudinal pulse magnetic fields during the third stage of conditioning from perpendicular magnetizing created by a four axis resonate frequency member comprising the third plurality of electromagnetic transducers with two axis of the four axis sequentially in opposite axis at a same time.

3. The apparatus for structuring water of claim 1 further comprising a second at least one permanent magnet associated with the third conduit and creating a second static magnetic field that is applied to the water when the water is traveling through the third conduit.

4. The apparatus for structuring water of claim 3 wherein the second at least one permanent magnet is positioned after the second electromagnetic transducer such that the second longitudinal pulse magnetic field is applied first to the water before the second static magnetic field is applied to the water.

5. The apparatus for structuring water of claim 1 further comprising a first filter disposed within the first internal water path.

6. The apparatus for structuring water of claim 5 further comprising a second filter disposed within the second internal water path.

7. The apparatus for structuring water of claim 2 further comprising a first filter disposed within the first internal water path, a second filter disposed within the second internal water path and a third filter disposed within the third internal water path.

8. The apparatus for structuring water of claim 1 wherein a frequency of an electromagnetic pulse generated by the first plurality of electromagnetic transducers, the first electromagnetic transducer, the second plurality of electromagnetic transducers and the second electromagnetic transducer is between 8 and 12 Hz.

9. The apparatus for structuring water of claim 8 further comprising a microprocessor in communication with the first plurality of electromagnetic transducers, the first electromagnetic transducer, the second plurality of electromagnetic transducers and the second electromagnetic transducer for controlling the frequency of the electromagnetic pulse.

10. The apparatus for structuring water of claim 9 further comprising a sensor or reader in communication with the water when the water is traveling through the second conduit, the sensor in communication with the microprocessor and based on information received from the sensor the microprocessor automatically adjusts the frequency of the electromagnetic pulse through adjustments to the first plurality of electromagnetic transducers, the first electromagnetic transducer, the second plurality of electromagnetic transducers or the second electromagnetic transducer.

11. The apparatus for structuring water of claim 5 wherein the first filter containing minerals or vitamins that are picked up or added to the water when the water travels through first filter.

12. The apparatus for structuring water of claim 1 wherein the water while traveling through the apparatus is subjected to simultaneous transversal and longitudinal pulse magnetic fields and strong permanent magnets over a water path direction in order to structure the water.

13. The apparatus for structuring water of claim 7 wherein the water while traveling through the apparatus is subjected to simultaneous transversal and longitudinal pulse magnetic fields and strong permanent magnets over a water path direction in order to structure the water; wherein the electromagnetic pulses and three stages of filtrations assist water purification and change solubility properties of the water resulting in a concentration of dissolved gases, changes in hydrogen bonding, changes in pH of the water for use in influencing cellular regeneration of living things who consume or absorbed the water that has traveled through the apparatus.

14. The apparatus for structuring water of claim 11 wherein the minerals added to the water comprise calcium, potassium, manganese and magnesium.

15. The apparatus for structuring water of claim 10 wherein the sensor or reader is a temperature sensor, photo sensor, barometric sensor, TSD (total solids dissolved in water) sensor ORP (oxidant reduction potential) sensor.

16. The apparatus for structuring water of claim 10 wherein the microprocessor is programmed with an algorithm that uses the information from the sensor or reader to automatically vary the frequency of the electromagnetic pulses and electromagnetic field intensities produced by the apparatus.

17. A method for structuring water, comprising steps of:
 a. creating a virtual electric current in water while the water is moving through a first static magnetic field created by a first permanent magnetic;
 b. directing the water to a first conditioning stage;
 c. perpendicularly magnetizing the water by a first transversal pulse magnetic field created by a four axis resonate frequency member comprising a first plurality of electromagnetic transducers while the water travels through the first conditioning stage;
 d. parallelly magnetizing subjecting the water by a first longitudinal pulse magnetic field created by a first electromagnetic transducer after the water leaves the first conditioning stage;
 e. directing the water to a second conditioning stage;
 e. perpendicularly magnetizing the water by a second transversal pulse magnetic field created by a four axis resonate frequency member comprising a second plurality of electromagnetic transducers while the water travels through the second conditioning stage;
 f. parallelly magnetizing the water by a second longitudinal pulse magnetic field created by a second electromagnetic transducer after the water leaves the second conditioning stage;
 g. directing the water to a third conditioning stage;
 h. perpendicularly magnetizing the water by a third transversal pulse magnetic field created by a four axis resonate frequency member comprising a third plurality of electromagnetic transducers while the water travels through the third conditioning stage;

i. parallelly magnetizing the water by a third longitudinal pulse magnetic field created by a third electromagnetic transducer after the water leaves the third conditioning stage; and j. subjecting the water to a second magnetic field created by a second permanent magnetic.

18. The method for structuring water of claim 17 further comprising a step of filtering the water is the water travels through the first conditioning stage.

19. The method for structuring water of claim 17 further comprising the steps obtaining information concerning the water after the water has left the first conditioning stage and automatically adjusting an electromagnetic pulse frequency for the transversal and longitudinal fields based on the information.

20. The apparatus for structuring water of claim 1 wherein an inner diameter of an exit end of the first internal water path is larger in size than an inner diameter of an exit end of the second internal water path.

\* \* \* \* \*